(12) United States Patent
Levkov et al.

(10) Patent No.: US 11,563,339 B2
(45) Date of Patent: Jan. 24, 2023

(54) REGULATED STORAGE CAPACITOR CHARGING DEVICE AND METHOD

(71) Applicant: Ramot at Tel Aviv University, Tel Aviv (IL)

(72) Inventors: Klimentiy Levkov, Tel Aviv (IL); Alexander Golberg, Tel Aviv (IL)

(73) Assignee: RAMOT AT TEL AVIV UNIVERSITY LTD., Tel Aviv (IL)

( * ) Notice: Subject to any disclaimer, the term of this patent is extended or adjusted under 35 U.S.C. 154(b) by 4 days.

(21) Appl. No.: 17/054,222

(22) PCT Filed: May 22, 2019

(86) PCT No.: PCT/IL2019/050576
§ 371 (c)(1),
(2) Date: Nov. 10, 2020

(87) PCT Pub. No.: WO2019/224819
PCT Pub. Date: Nov. 28, 2019

(65) Prior Publication Data
US 2021/0249893 A1 Aug. 12, 2021

Related U.S. Application Data

(60) Provisional application No. 62/675,921, filed on May 24, 2018.

(51) Int. Cl.
*H02J 7/34* (2006.01)
*H02J 7/00* (2006.01)
*C12M 1/42* (2006.01)

(52) U.S. Cl.
CPC ........ *H02J 7/345* (2013.01); *H02J 7/007182* (2020.01); *C12M 35/02* (2013.01); *H02J 2207/50* (2020.01)

(58) Field of Classification Search
CPC .. H02J 7/345; H02J 7/007182; H02J 2207/50; H02J 7/007184; H02J 7/06;
(Continued)

(56) References Cited

U.S. PATENT DOCUMENTS 6,799,002 B2 * 9/2004 Birumachi ......... G03G 15/2003
399/330
8,525,487 B1 * 9/2013 Stevenson ............. H02J 7/0063
320/166
(Continued)

FOREIGN PATENT DOCUMENTS

AT 404415 B * 9/1998 ............ H02M 7/217
CN 206180984 U 5/2017
(Continued)

OTHER PUBLICATIONS

Anonymous: "Cockcroft-Walton generator"—Wikipedia.
(Continued)

*Primary Examiner* — M Baye Diao
(74) *Attorney, Agent, or Firm* — Emerson, Thomson & Bennett, LLC; Roger D. Emerson

(57) ABSTRACT

A device and method are disclosed for regulated storage capacitor charging to high voltage. The device comprises an AC source configured to output an AC voltage, a voltage multiplier that constitutes a charging unit and a control unit. The control unit is configured to constantly sense the voltage on the storage capacitor and upon detecting that a predefined maximum charging voltage has been reached to react in at least one of the following ways: stop charging the storage capacitor, and closing an output switch so as to discharge of the storage capacitor through some load. The capacitance of each capacitor in the charging unit is substantially smaller
(Continued)

than that of the storage capacitor so as achieve accurate maximum charging voltage as well as limited charging current.

5 Claims, 2 Drawing Sheets

(58) Field of Classification Search
 CPC .......... C12M 35/02; C12N 13/00; A61N 1/08; A61N 1/327; A61N 1/025; H03K 3/53
 USPC ......................................................... 320/166
 See application file for complete search history.

(56) References Cited

U.S. PATENT DOCUMENTS

| | | | |
|---|---|---|---|
| 9,609,710 B2 * | 3/2017 | Ido | H05B 45/48 |
| 9,859,792 B2 * | 1/2018 | Wang | H02M 3/07 |
| 10,148,128 B2 * | 12/2018 | Murayama | H02M 3/33573 |
| 10,404,176 B2 * | 9/2019 | Hu | H02M 3/07 |
| 2007/0231873 A1 | 10/2007 | Ragsdale | |
| 2015/0349641 A1 * | 12/2015 | Smith | H02M 1/32 323/271 |

FOREIGN PATENT DOCUMENTS

| | | | | |
|---|---|---|---|---|
| CN | 104993182 B | * | 1/2018 | ............ H02J 7/0052 |
| EP | 3176246 A1 | | 6/2017 | |
| GB | 2491475 A | | 12/2012 | |
| KR | 20130129584 A | * | 11/2013 | ........ H02M 3/33507 |
| RU | 2364021 C1 | | 8/2009 | |

OTHER PUBLICATIONS

EESR issued Sep. 7, 2021 (6 pages).
International Search Report and Written Opinion for corresponding PCT App. No PCT/IL2019/050576 dated Sep. 5, 2019. 4 pages.

* cited by examiner

US 11,563,339 B2

REGULATED STORAGE CAPACITOR CHARGING DEVICE AND METHOD

FIELD OF THE INVENTION

The present invention relates generally to high voltage energy storage capacitor charging, and more particularly, to methods and systems for controlled charging of storage capacitor in electroporation applications.

BACKGROUND OF THE INVENTION

There are various circuit models in the art for charging energy storage capacitor (ESC) to high voltage, i.e. above 5 KV. A typical application of these circuits is to generate a short and very strong pulsed electric field (PEF). This PEF is used, for example, to result in an electroporation process in an Electroporation Cell (EPC).

One favorable charging circuit model is disclosed in European Patent Application EP3176246. This prior art publication provides an electric pulse generator for an electroporator including, as a poring pulse generating means: (A) an n-stage Cockroft-Walton circuit; and (B) a branching-merging circuit including (b1) a switching switch that is turned off in a high-voltage mode and turned on in a low-voltage mode; and (b2) a circuit that is m1-series m2-parallel capacitors connected in series to the output side of the switching switch. However, in this publication there is no mention of how to adjust the amplitude of the generated pulse.

Thus, it would be desirable to provide a simple to implement technique for ESC charging when high amplitude PEF is required, when accurately adjustable amplitude is required as well as limited peak EPC charging current.

SUMMARY OF THE INVENTION

Accordingly, it is a principal object of the present invention to provide a device and method for storage capacitor charging to high voltage, while assuring limited peak charging current as well as accurate maximum charging voltage. Thus, in accordance with an embodiment of the present invention, the disclosed device comprises an AC source configured to output an AC voltage, a voltage multiplier that constitutes a charging unit and a control unit. In typical embodiments the voltage multiplier is structured as an N-stage Cockroft-Walton circuit whose internal capacitors serve as charging capacitors. The control unit is configured to constantly sense the voltage on the storage capacitor and upon detecting that a predefined maximum charging voltage has been reached to react in at least one of the following ways: stop charging the storage capacitor, and closing an output switch so as to discharge of the storage capacitor through some load. The capacitance of each charging capacitor is substantially smaller than that of the storage capacitor so as achieve accurate maximum charging voltage as well as limited charging current.

In some embodiments the storage capacitor constitutes an integral part of the charging device, and the AC source comprises a step-up transformer.

The control unit is further configured in typical embodiments to decrease the frequency of the AC source upon detecting that the storage capacitor voltage has reached a predefined distance from the predefined maximum charging voltage so as to improve the adjustment accuracy of the maximum charging voltage.

In some applications of the disclosed charging device the load through which the storage capacitor is discharged is an Electroporation Cell (EPC).

In accordance with an embodiment of the present invention, there is also provided a method of charging an energy storage capacitor to a predefined maximum charging voltage, the method comprises the following steps: Charging the storage capacitor by means of an AC source and a charging unit comprising an N-stage Cockroft-Walton circuit (N represents any integer of 1 or more), wherein the capacitance of each capacitor in the charging unit is substantially smaller than that of the storage capacitor. Constantly sensing the voltage on the storage capacitor. And as a last step, upon detecting that the predefined maximum charging voltage has been reached, reacting in at least one of the following ways: stop charging the storage capacitor, and discharging the storage capacitor through a load.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Embodiments of the present invention provide regulated energy storage capacitor charging devices, wherein high charging voltage is required. A typical embodiment comprises an AC source and one or more charging stages that form an N-stage Cockroft-Walton circuit (N represents any integer of 1 or more). Each charging stage provides for rectifying and stepping-up the AC source voltage as well as for transferring a small amount of charge to the storage capacitor in each period of the AC source. Employing in the charging stages charging capacitors with substantially small capacitance relative to the storage capacitor's results in limited charging current consumption from the AC source at the expense of multiple periods thereof. It can be shown that the number of periods is very roughly equal to the above capacitance ratio. This way the exact maximum charging voltage is adjusted in typical embodiments by the charging time. Another advantage provided by embodiments of the present invention is that the peak current consumed from the AC source while charging the storage capacitor is proportional to and limited by the charging capacitor's capacitance, i.e. it decreases as the capacitance decreases. This proportion also holds when the storage capacitor is abruptly discharged to generate a pulsed electric field (PEF) e.g. in electroporation applications.

Figure 1:
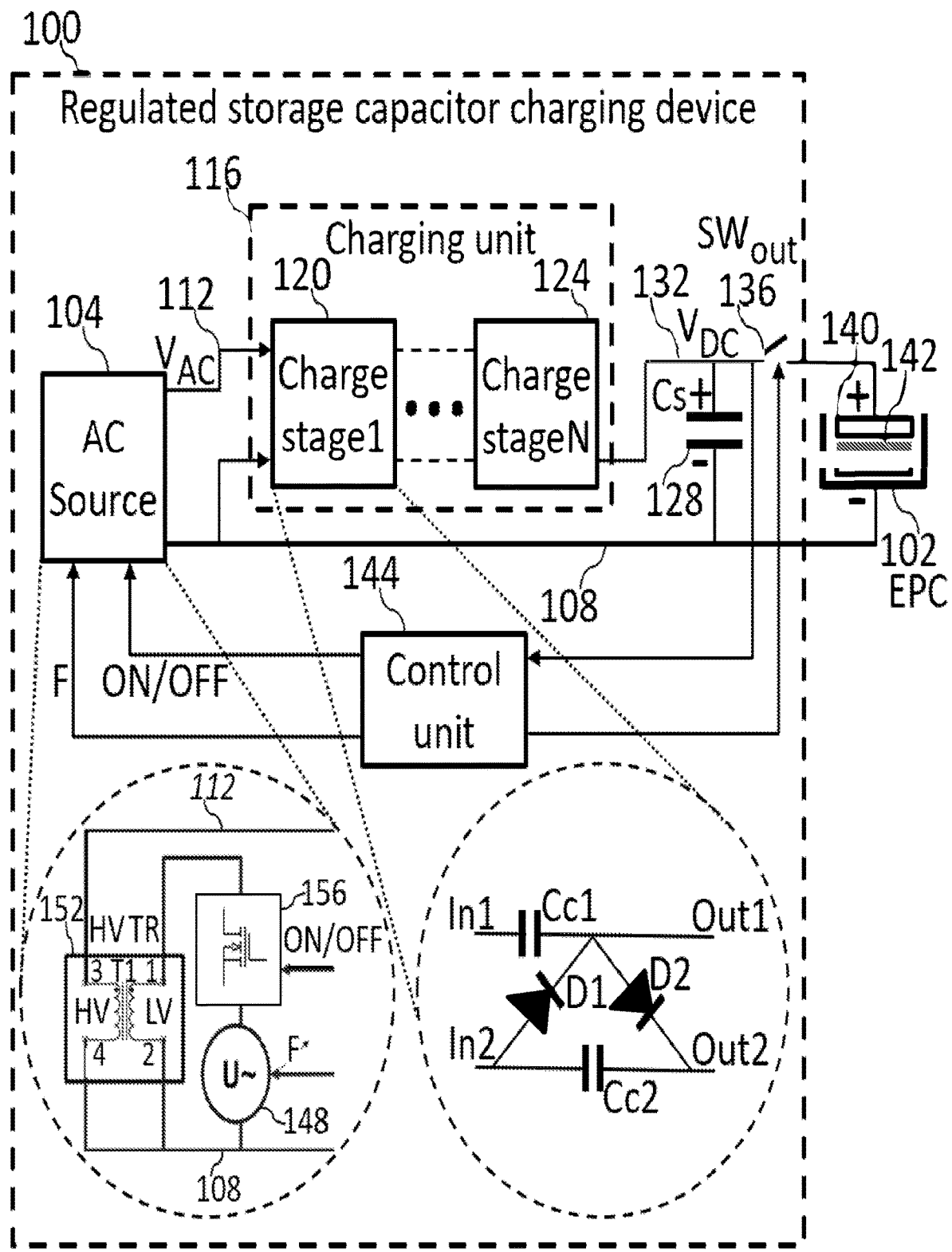
FIG. 1 is a circuit diagram that schematically illustrates a regulated storage capacitor charging device, in accordance with an embodiment of the present invention.

Referring to FIG. 1, there is shown a circuit diagram that schematically illustrates a regulated storage capacitor charging device (in short 'charging device') 100, in accordance with an embodiment of the present invention. Charging device 100 is connected to a load 102 which is described below. Charging device 100 comprises an AC source 104 which outputs an AC voltage $V_{AC}$ between a common line 108 and an output terminal 112 thereof. Load 102 is also connected to common line 108. $V_{AC}$ feeds a charging unit 116 comprising N charging stages indicated in FIG. 1 by reference numerals 120 to 124. In typical embodiments charging unit 116 forms an N-stage Cockroft-Walton voltage multiplier circuit. In other embodiments other voltage multiplier schemes can be used such as switched-capacitor and charge pump. In a simple embodiment of the present invention only charging stage 120 is implemented. Charging unit 116 outputs a charging current through an output line 132. The charging current charges an energy storage capacitor (in short storage capacitor) 128 denoted as Cs. Consequently, Cs 128 is charged to a voltage $V_{DC}$, which constantly grows during the charging process. In some embodiments, Cs 128 is an integral part of charging device 100 whereas in other embodiments Cs 128 is pluggable to charging device 100 so as to suit the specific application. $V_{DC}$ may reach in some applications a maximum value $V_{DC-max}$ of 5 KV to 10 KV, however higher $V_{DC}$ can be achieved in embodiments of the disclosed techniques. It can be easily shown that $V_{DC-max}$ is close to $2N*V_{AC-peak}$.

Charging device 100 further comprises an output switch 136, denoted as SWout, connected on output line 132. SWout 136 is intended to connect and disconnect load 102 to Cs 128. When SWout 136 is closed Cs 128 is discharged through load 102 thereby exerting a short and very strong pulsed electric field (PEF) on load 102. In the described embodiment, the PEF results in an electroporation process in an Electroporation Cell (EPC) 102, which comprises gravitation press electrodes 140 and biomass 142 that shall be subject to electric field fractionation. In various embodiments either electro-mechanical switch or semiconductor based switch is employed as SWout 136. Cs 128 is typically a film capacitor owing to the high $V_{DC-max}$.

A control unit 144 controls the operation of charging device 100. In particular, it turns ON/OFF AC source 104. When control unit 144 turns AC source 104 ON, $V_{DC}$ starts to build up through charging unit 116. Control unit 144 constantly senses output line 132. When it detects that $V_{DC}$ has reached a predefined $V_{DC-max}$ it stops increasing $V_{DC}$ by either one of the following ways or by performing both of them:

(a) It stops charging Cs 128 by turning OFF AC source 112. In some embodiments the charging is stopped by opening an additional switch on the charging path (not shown in FIG. 1).
(b) It closes SWout 136, thereby causing Cs 128 to discharge through EPC 102.

In some embodiments, control unit 144 also decreases the frequency of AC source 104 once $V_{DC}$ becomes quite close to the predefined $V_{DC-max}$. This is done to improve the $V_{DC-max}$ adjustment accuracy. The frequency decrease factor is typically ten or more and it is typically applied at a voltage distance of ten percent or less from the predefined $V_{DC-max}$. In one embodiment, control unit 144 comprises a general purpose microcontroller which runs software for carrying out the above functions as well as some more application specific functions e.g. desired PEF patterns. However, other implementation technologies can be used alternatively or additively such as ASICs and FPGAs.

Following are more detailed description of AC source 104 and each charging stage such as 120 as implemented in one embodiment. An AC generator 148 within AC source 104 is a square wave oscillator typically having a frequency of some tens of KHz. This frequency can be adjusted by control unit 144 as described above. The output signal of AC generator 148 is applied to a primary winding of a switching ferrite core transformer 152 through a MOSFET switch 156. Switch 156 serves for turning ON/OFF AC source 104 by control unit 144. Transformer 152 steps-up generator 148 output signal so as to feed charging unit 116 with a signal peak of a few KV.

Let us refer now to the zoomed-in structure of charging stage 120. It has first and second input terminals denoted In1 and In2 respectively, and first and second output terminals denoted Out1 and Out2 terminals respectively. A first charging capacitor Cc1 is connected between In1 and Out1 terminals. A second charging capacitor Cc2 is connected between In2 and Out2 terminals. Cc2 is actually redundant in a charging stage that is the last one and/or the only one in charging unit 116. This is since in this case Cc2 is connected in parallel with Cs 128. Cc1 and Cc2 are typically of equal capacitance which is substantially small relative to Cs 128. A minimum capacitance ratio is 10, however in typical embodiments the ratio is larger 100, e.g. Cc1=Cc2=0.047 µF and Cs 128=100 µF. Larger Cc1 and Cc2 are typically employed when the number of charging stages N>1.

Charging stage 120 further comprises switching elements. A first switching element, which is diode D1 in the depicted enablement, is connected between Out1 and In2 terminals. A second switching element, which is diode D2, is connected between Out1 and Out2 terminals. D1 is connected such that it conducts only when In2-to-Out1 voltage>0, and D2 is connected such that it conducts only when Out1-to-Out2 voltage>0. For achieving a negative $V_{DC}$ diodes D1 and D2 are inversely connected. In some embodiments, other semiconductor first and second switching elements are employed instead of diodes D1 and D2 respectively, which are driven by control unit 144 to conduct according to the above conducting rules of D1 and D2. In some embodiments two charging units if inverse polarities are employed so as to double the produced $V_{DC}$.

In1 and In2 terminals of the first charging unit are connected to AC source output terminal 112 and common line 108 respectively. Out2 terminal of the last charging unit is connected to output line 132. If several charging units are employed they are connected in series such that for each pair thereof Out1 and Out2 terminals of the preceding stage are connected to In1 and In2 terminals of the following stage respectively.

The above description has focused on the specific elements of charging device 100 that are essential for understanding certain features of the disclosed techniques. Conventional elements and connections that are not needed for this understanding have been omitted from FIG. 1 for the sake of simplicity, but will be apparent to persons of ordinary skill in the art. The configuration shown in FIG. 1 is an example configuration, which was chosen purely for the sake of conceptual clarity. In alternative embodiments, any other suitable configurations can also be used.

Figure 2:
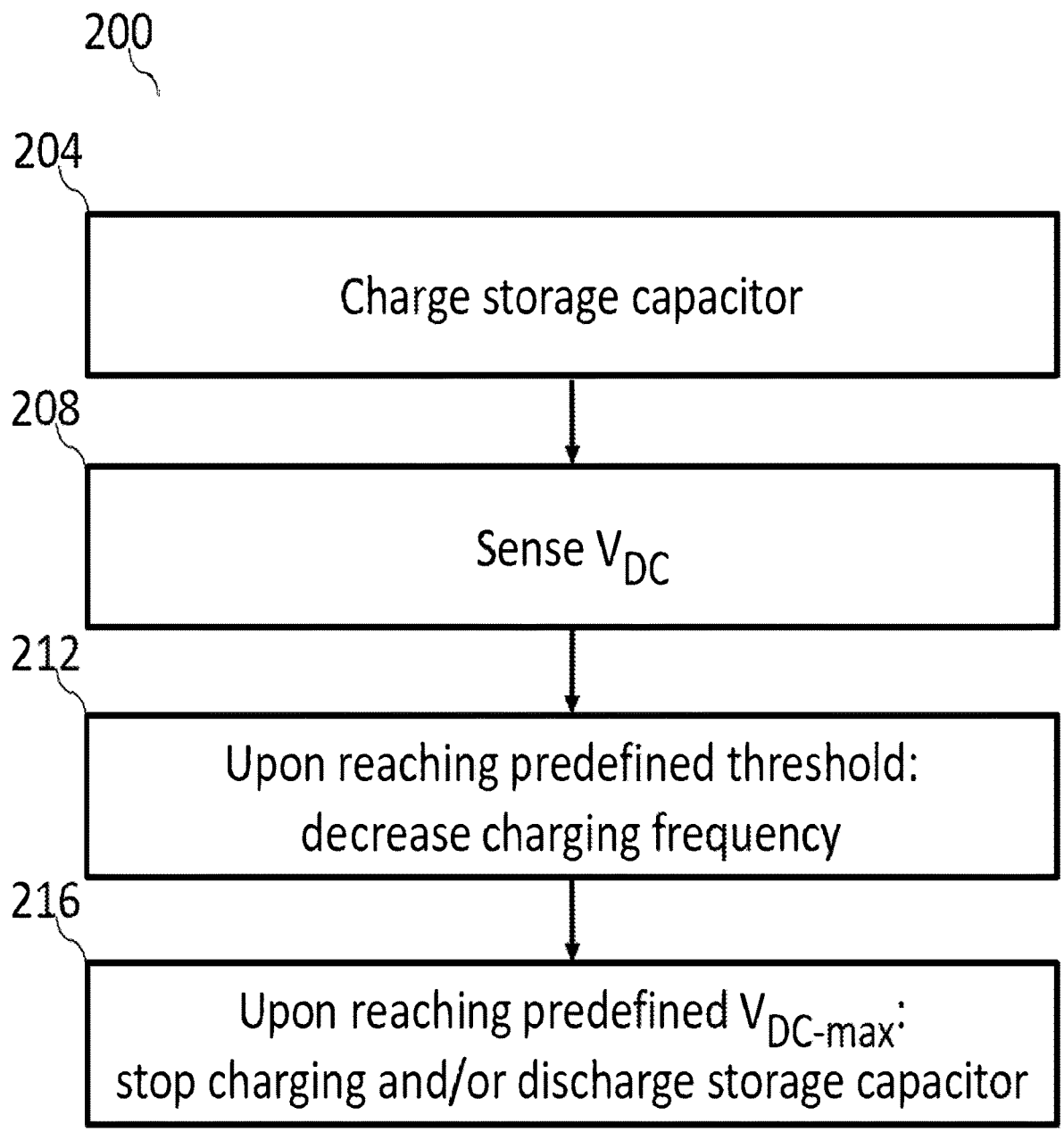
FIG. 2 is a flowchart that schematically illustrates a method of charging an energy storage capacitor to a predefined high charging voltage, in accordance with an embodiment of the present invention.

Referring now to FIG. 2, there is shown a flowchart 200 that schematically illustrates a method of charging an energy storage capacitor to a predefined high charging voltage $V_{DC-max}$, in accordance with an embodiment of the present invention. Flowchart 200 begins with a charging step 204, in which charging device 100 charges storage capacitor Cs 128 as explained above. In a sensing step 208, control unit 144 constantly senses $V_{DC}$ as explained above. In a decreasing step 212, control unit 144 decreases the frequency of AC generator 148 upon sensing that a predefined threshold has been reached, as explained above, for fine tuning $V_{DC-max}$. Flowchart 200 ends with a stop step 244, in which control unit 144 causes charging device 100 to stops charging Cs 128 by either turning OFF AC source 112 and/or discharging Cs 128 through SWout 136.

Flowchart 200 is an example flowchart, which was chosen purely for the sake of conceptual clarity. In alternative embodiments, any other suitable flowchart can also be used for illustrating the disclosed method. Method steps that are not mandatory for understanding the disclosed techniques were omitted from FIG. 2 for the sake of simplicity.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A regulated storage capacitor charging device comprising:
   an output line and a common line for connecting therebetween an energy storage capacitor that has to be charged to a predefined maximum charging voltage;
   an AC source configured to output an AC voltage between the common line and an output terminal thereof;
   a charging unit comprising an N-stage Cockroft-Walton circuit, N representing any positive integer, first and second terminals thereof connected to the output terminal of the AC source and to the common line respectively and an output terminal thereof connected to the output line, wherein the capacitance of each capacitor in the charging unit is substantially, smaller than that of the storage capacitor to be charged;
   an output switch operatively coupled to connect and disconnect a load to the storage capacitor; and
   a control unit configured to constantly sense the voltage on the storage capacitor, upon detecting that a predefined maximum charging voltage has been reached to react in at least one of the following ways:
   (a) stop charging the storage capacitor, and
   (b) closing the output switch so as to discharge the storage capacitor through the load,
   wherein the control unit is further configured to decrease the frequency of the AC source, by a factor of ten or more, upon detecting that the voltage on the storage capacitor has reached a predefined distance from the predefined maximum charging voltage so as to improve the accuracy of a resulting maximum charging voltage.

2. The charging device of claim 1, wherein the storage capacitor constitutes a part thereof.

3. The charging device of claim 1, wherein the AC source comprises a step-up transformer.

4. The charging device of claim 1, wherein the load is an Electroporation Cell (EPC).

5. A method of charging an energy storage capacitor to a predefined maximum charging voltage, the method comprising the steps of:
   charging the storage capacitor by means of an AC source and a charging unit comprising an N-stage Cockroft-Walton circuit, N representing any positive integer, wherein the capacitance of each capacitor in the charging unit is substantially smaller than that of the storage capacitor;
   constantly sensing the voltage on the storage capacitor;
   upon detecting that the predefined maximum charging voltage has been reached, reacting in at least one of the following ways:
   (a) stop charging the storage capacitor, and
   (b) discharging the storage capacitor through a load; and
   decreasing the frequency of the AC source, by a factor of ten or more, upon detecting that the storage capacitor voltage has reached a predefined distance from the predefined maximum charging voltage, so as to improve the accuracy of a resulting maximum charging voltage.

* * * * *